United States Patent [19]

Rubinstein

[11] 4,286,596
[45] Sep. 1, 1981

[54] TAMPON CONTAINING A LIQUID MEDICANT

[75] Inventor: Morton K. Rubinstein, Pacific Palisades, Calif.

[73] Assignee: Herbert Rubinstein, Santa Cruz, Calif.

[21] Appl. No.: 881,651

[22] Filed: Feb. 27, 1978

[51] Int. Cl.³ .............................................. A61F 13/20
[52] U.S. Cl. ................................................... 128/270
[58] Field of Search ............... 128/261, 269, 270, 271, 128/285

[56] References Cited
U.S. PATENT DOCUMENTS

| | | | |
|---|---|---|---|
| 592,659 | 10/1897 | Miller et al. | 128/261 |
| 823,499 | 6/1906 | Barlow | 128/261 |
| 1,561,020 | 11/1925 | Pond | 128/270 |
| 1,887,526 | 11/1932 | Spielberg et al. | 128/270 |
| 2,333,342 | 11/1943 | Slocumb | 128/271 |
| 2,440,141 | 4/1948 | Donovan | 128/285 |
| 2,579,403 | 12/1951 | Slomowitz et al. | 128/269 |
| 2,629,381 | 2/1953 | Brown | 128/270 |
| 3,512,527 | 5/1970 | Desoye et al. | 128/261 |
| 3,521,637 | 7/1970 | Waterbury | 128/270 |
| 3,690,321 | 9/1972 | Hirschman | 128/285 |

Primary Examiner—C. Fred Rosenbaum
Attorney, Agent, or Firm—Jack M. Wiseman; Francis W. Anderson

[57] ABSTRACT

A tampon comprising a rigid conical end for entry into the cavity of a body. Extending from the base of the conical end is a bulb-shaped body made of highly absorbable and expansible material. Disposed within the tampon body is a rupturable container holding a liquid medicant. Immediately before or during the insertion of the tampon into the cavity of the body, the container is ruptured, releasing the liquid medicant to be absorbed by the tampon body. After the tampon body is inserted into the cavity of the body, the tampon body expands radially about the longitudinal axis thereof from the absorption of the liquid medicant. The lips of the cavity of the body grasp the neck of the tampon body and the expanded tampon body engage the walls surrounding the cavity of the body inwardly of the lips for inhibiting unintentional expelling of the tampon from the cavity of the body and for providing direct contact between the medicated tampon body and the walls surrounding the cavity of the body.

10 Claims, 5 Drawing Figures

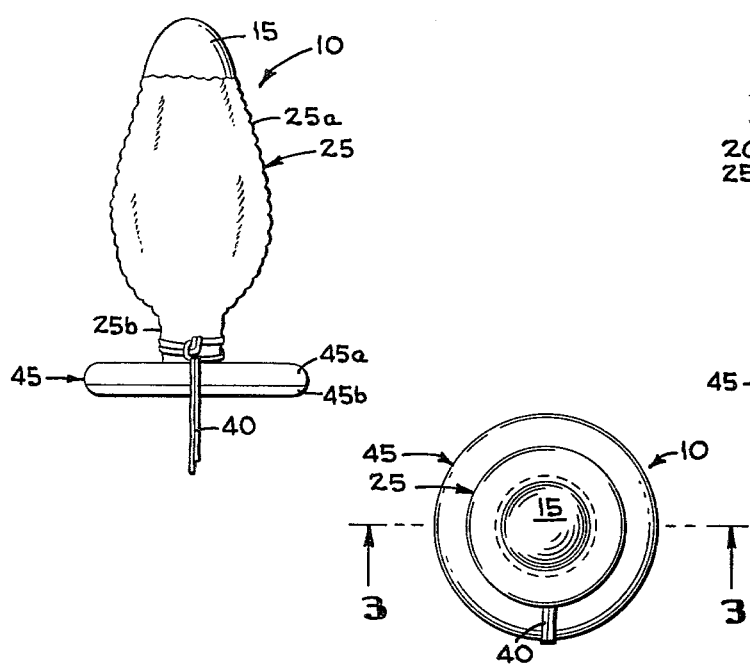
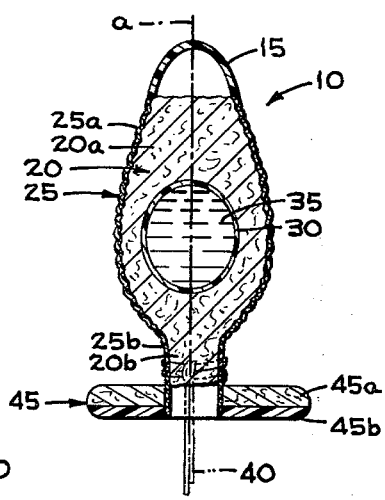
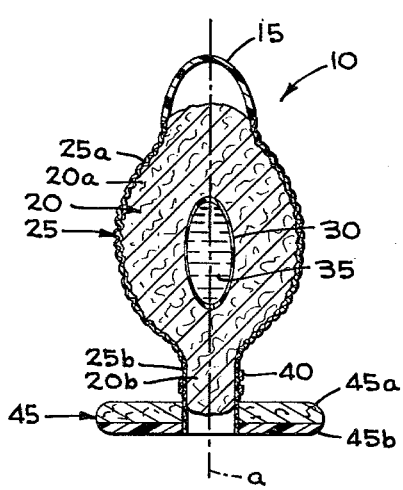
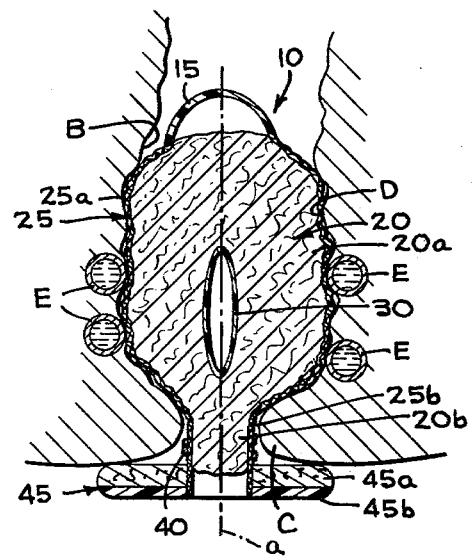

TAMPON CONTAINING A LIQUID MEDICANT

BACKGROUND OF THE INVENTION

The present invention relates in general to tampons, and more particularly to a tampon having a container of liquid medicant disposed therein.

The use of tampons to absorb body fluids such as intravaginal tampons to absorb menstrual blood is in common practice. Somewhat less common, but never the less important, use of tampons is in the application of medication to specific areas of the body. For instance, intravaginal suppositories and tampons are commonly used to apply medication to that area for specific yeast and other infections to which the vagina is subject.

The present invention concerns an improvement in the manner in which medicated tampons may be applied to a specific body area. Although it is intended primarily for rectal use in the care of hemorrhoids and rectal fistula, it may also be used to advantage in other body cavities, such as the vagina, uterus, external auditory canal, etc.

Hemorrhoids is one of the most common afflictions of man. It can often be treated medically by the direct application of certain medicines such as local anesthetics, astringents, corticosteroids, et cetera, directly to the enlarged veins comprising the hemorrhoids. It is apparent that direct application of such medication, acting for a prolonged period of time (such as over a period of many hours), would be advantageous. However, the presently available medication is usually supplied as a local ointment or as a suppository. The disadvantages of the former are that it is messy and does not reach internal hemorrhoids (those within the rectum), thus not affecting the most common form of hemorrhoids. The disadvantage of the latter is that it is also messy and when inserted into the rectum, the suppository quickly melts and disperses in the vicinity of the hemorrhoids, but most of the medication is lost in the rectal vault and thus not available to the hemorrhoidal tissue for a period of time long enough to be most effective. Further, the medicine which is applied to the enlarged veins by this method is quickly diluted by body fluids, thus reducing the efficacy of the medication.

In the patent to Slomowitz et al., U.S. Pat. No. 2,579,403, there is disclosed a tampon having a gauze pad body. Disposed in the gauze pad body is a container of medicine. The container of medicine is ruptured and the medicine oozes into the absorbent gauze pad.

The patent to Pond U.S. Pat. No. 812,769, discloses a medicated tampon having a conical end for entry into a cavity of a body. Disposed in the conical entry end of the tampon is a medicant. Extending from the conical end of the tampon is a body of absorbent, expansible material. The filling is subjected to water for expanding the same before the tampon is inserted into the cavity of the body. The expansion of the tampon body from absorbing water causes the tampon body to engage the walls surrounding the cavity of the body to prevent the tampon from slipping out from the cavity of the body prematurely.

The patent to Hartop, U.S. Pat. No. 3,865,108, discloses a tampon in which a container of medicant is disposed in the body of the tampon. After the tampon is inserted into the cavity of a body, the body of the tampon absorbs body fluids, causing the body of the tampon to expand. As a consequence thereof, the container for the medicant collapses to dispense the medicant into the cavity to the body. An enlarged section is formed at the end of the tampon body to limit the extent of the insertion of the tampon into the body cavity.

In the patent to Waterbury, U.S. Pat. No. 3,521,637, there is disclosed a tampon having a body made of absorbent material. Disposed within the tampon body is a container holding a suitable vitamin in a liquid. The container is ruptured by exertion of finger pressure or the application of a mechanical force before the tampon is inserted into the cavity of the body. The patent to Spielberg et al., U.S. Pat. No. 1,887,526, discloses a medical tampon having a conical entry end. Extending from the base of the conical entry end is a body of absorptible material. Contained by the conical entry end is a fluid medicant. After the tampon is inserted into the cavity of the body, the conical entry end dissolves from body fluids.

The patent to Austin, Jr., U.S. Pat. No. 3,486,504, discloses a device containing an absorbent cotton body. A capsule containing medication is disposed within the cotton body. By squeezing the cotton body, the capsule is ruptured to release the medicant into the cotton body for application to an infected area. A flange is formed at the end of the body to surround an infected area. The patent to Hochstrasser et al., U.S. Pat. No. 3,515,138, shows a tampon having an absorbable body. A medicant is contained in the tampon body. After the tampon is inserted into the cavity of the body, the medicant melts at body temperature.

Other patents of interest are:
U.S. Pat. No. 3,512,527
U.S. Pat. No. 1,879,307

Applicant had filed on Dec. 4, 1975, Ser. No. 637,599, an application entitled "Medicated Tampon", which application has been abandoned.

SUMMARY OF THE INVENTION

A tampon comprising an entry end and a bulb-shaped body of absorbable expansible material extending from the proximal portion of the entry end. Disposed within the body is a rupturable container of liquid medicant. Before or during the insertion of the tampon into the cavity of the body, the container is ruptured to release the liquid medicant. After the tampon has been inserted into the cavity of the body, the liquid medicant is absorbed by the tampon body for expanding the tampon body radially about the longitudinal axis of the tampon. The lips of the cavity of the body grasp the neck of the tampon body and the expanded tampon body engages the walls surrounding the cavity of the body to apply the medicant directly to the walls surrounding the cavity of the body and to inhibit the inadvertent expulsion of the tampon from the cavity of the body.

A medicated tampon that serves to keep the medication applied against the enlarged hemorrhoidal veins for a prolonged period of time, thus increasing the effectiveness of the treatment. It is also much less messy.

Rectal tampons have not been popular because they have a tendency to be extruded from the rectal vault with body movement such as sitting, standing, walking, urinating, coughing, and other maneuvers that tend to increase intra-abdominal pressure. Furthermore, currently available tampons are generally medicated by applying creams or jells and other viscous materials to the surface of the tampon. This tends to reduce the accuracy and specificity of the available medications. The present invention not only prevents or minimizes unintentional expulsion of the tampon from the body cavity, but provides a means where aqueous medication may be freshly applied to the intended area. This allows for a more precise concentration of medication to be applied to the appropriate region. It also allows the medication to be available for use when required without evaporation or destruction by oxidation while awaiting usage.

A feature of the present invention is that it involves a tampon which is provided with a means of enlarging the intracavity end of the tampon after it is in place within the body so that body movements will have a reduced tendency to force unintentional protrusion or ejection of said tampon. The tampon also takes the shape of the body cavity, increasing contact between tampon and mucosal surface. A further feature of this invention is to provide a means of applying medicated tampons to a body cavity whereby the medication so applied may be in liquid form, if desired.

An object of the present invention is to provide a means whereby the medication to be used can be held in liquid form without evaporation or degradation because of exposure to air until such time as its use is required.

BRIEF DESCRIPTION OF THE DRAWINGS

FIG. 1 is a schematic side elevation view of a tampon embodying the present invention.

FIG. 2 is a diagrammatic plan view of the tampon shown in FIG. 1.

FIG. 3 is a longitudinal section view of the tampon shown in FIGS. 1 and 2, taken along line 3—3 of FIG. 2 before the container holding medicant, which is disposed in the tampon body, has been ruptured.

FIG. 4 is a longitudinal section view of the tampon shown in FIGS. 1 and 2 taken along line 3—3 of FIG. 2 after the container holding the medicant has been ruptured and has been absorbed by the tampon body.

FIG. 5 is a longitudinal section view of the tampon shown in FIGS. 1 and 2 taken along line 3—3 of FIG. 2 after the container holding the medicant has been ruptured and has been absorbed by the tampon body and illustrated disposed within the rectal vault of a body.

DESCRIPTION OF THE PREFERRED EMBODIMENT

Illustrated in FIGS. 1-3 is the tampon 10 embodying the present invention. The tampon 10 comprises a conical end 15, which is sufficiently rigid and which is suitably configured for entry into the cavity of a body. In the exemplary embodiment, the conical end 15 is made of a suitable plastic material. While the conical end 15 is shown to be hollow, it is apparent that it could be a solid member or be of any suitable shape for entry into the cavity of a body. The entry end 15 may be prelubricated in a well-known manner to facilitate the insertion thereof into the cavity of the body.

Extending from the base of the entry end 15 is a bulb-shaped body 20 (FIGS. 3-5), which is made of a highly liquid absorbable and expansible material. In the preferred embodiment, the bulb-shaped tampon body 20 is made of cotton. The bulb-shaped tampon body 20 includes an ovate section 20a and a neck section 20b.

Surrounding the bulb-shaped tampon body 20 is a liquid absorbable envelope 25, which is made of a loose web of material, such as cotton gauze. Mesh material of silk, nylon or the like may also be employed. The envelope 25 serves to contain the bulb-shaped tampon body and to limit the extent of the expansion of the bulb-shaped tampon body 20. While the envelope 25 is shown to be a loose web surrounding the bulb-shaped tampon body 20, it is apparent that it may be an outer skin or layer thereof. The envelope 25 includes an ovate section 25a and a neck section 25b.

Disposed within the bulb-shaped tampon body 20 is a rupturable container 30. The container 30 is preferably made of a suitable thin plastic film material so as to be rupturable by applying manual force thereto or by the application of a mechanical force. Disposed within the container 30 is a suitable liquid medicant 35 (FIG. 3).

Before or during the insertion of the tampon 10 into the cavity of a body, the container 30 is ruptured by pinching the walls of the tampon body 20 or by the act of inserting the tampon 10 into the cavity of a body. Alternatively, the container 30 can be ruptured mechanically before or during the insertion of the tampon 10 into the cavity of a body by a cardboard or plastic inserter, not shown. Such inserters are in the form of a tube and are well-known in the tampon art. The inserter is placed into an opening of the neck 25b to also aid in the insertion of the tampon 10 into the cavity of a body.

Before or during the insertion of the tampon 10, the container 30 for the liquid medicant 35 is ruptured to release the liquid medicant. After the tampon 10 is inserted into the cavity of the body, the liquid medicant is absorbed by the tampon body 20. As a consequence thereof, the tampon body 20 expands radially outward about the longitudinal axis a of the tampon body 20 (FIG. 4). The tampon body 20 retains its shape for a short interval of time between the time of rupturing the container 30 to release the liquid medicant 35 and the time of full radial expansion of the tampon body 20. It is estimated that the time interval would be in the vicinity of several seconds. This would allow, generally, sufficient time to enable the tampon 10 to be inserted into the cavity of a body with ease.

It is apparent that a plurality of containers 30 could be employed with each container, respectively holding various medicants and various concentrations of the same medicant.

It is to be observed that the neck 20b of the tampon body 20 is made of highly absorbable and expansible material as is the ovate portion 20a of the tampon body 20. Also, the neck portion 25b of the envelope 25 surrounds the neck portion 20b of the tampon body 20 as does the ovate portion 25b of the envelope 25 surrounding the ovate portion 20a of the tampon body 20. Thus, the neck portion 20b of the tampon body 20 expands radially upon the absorption of the liquid medicant 35 in a manner similar to that for the expansion of the ovate portion 20a of the tampon body 20 upon the absorption of the liquid medicant 35.

A string or cord 40 (FIG. 1) is firmly attached to the neck portion 25b of the envelope 25. The string or cord 40 is of sufficient length to remain outside the cavity of the body when the tampon 10 is inserted in the cavity of the body to be grasped for the removal of the tampon 10 from the cavity of the body.

A disc protector 45 is integrally formed with the neck portion 25b of the envelope 25 and the neck portion 20b of the tampon body 20 at the distal end thereof. The disc protector 45 comprises an absorbent portion 45a made of cotton or other suitable absorbent material and an impervious portion 45b made of plastic or other suitable impervious material. The impervious portion 45b forms a skin or an outside layer for the absorbent portion 45a.

The absorbent portion 45a faces the body cavity, such as the anus, to protect the user from escaping substances to reduce the soiling of clothes or the like.

After the tampon 10 has had its container 30 ruptured for the absorption of the liquid medicant by the bulb-shaped tampon body 20 and after the tampon 10 is inserted into the body cavity B, such as the anal vault (FIG. 5), the bulb-shaped tampon body 20 expands radially outward from the longitudinal axis a of the tampon 10. The tampon 10 was inserted into the body cavity B through the lips C of the body cavity B, such as the anal sphincter for the anal vault. The medicant container 30 has been ruptured by previously squeezing the body 20 of the tampon 10 just prior to insertion, or by means of the force needed to insert the tampon 10 into the body cavity B, or by means of a mechanical inserter, not shown. On inserting the tampon 10, force is applied to the medicant container 30 causing it to rupture, expelling the medicant 35 contained by the container 30 and allowing the tampon body 20 to expand radially after a few seconds. The ruptured medicant container 30 is depicted in FIG. 4 showing the partially empty medicant container 30 and the expanded tampon body 20 with the now more tightly held web envelope 25 limiting the shape and the extent of the expansion of absorbent tampon body 20.

The neck 20b of the tampon body 20 has also expanded because of the absorption of the medicant 35 contained in the container 30. The expanded necks, such as the neck 25b of the envelope 25 and the neck 20b of the tampon body 20, are now grasped firmly by the lips C of the body cavity, such as the anal sphincter. The protector 45 and the pull cord 40 extending beyond the lips C, such as the anal sphincter, are in place.

The radial expansion of the tampon body 20 of the tampon 10 allows direct contact between the medicated absorbent material, such as the ovate portion 25a of the envelope 25 and the ovate portion 20a of the tampon body 20, and the walls D surrounding the body cavity B. When the walls D surrounding the body cavity B includes enlarged veins, such as the internal hemorrhoids E, there is intimate contact between the hemorrhoids and the medicated absorbent material. The soft, expanded body 20 of tampon 10 configures to the shape of the hemorrhoidal veins, allowing intimate contact between the medicant and hemorrhoids.

The absorbent portion 45a of the protector 45 becomes moistened with medicant through the absorbent material of the neck portion 20b, thus providing contact with external hemorrhoids should any be present.

It is apparent from the foregoing description that the subject invention provides an improved tampon for insertion into body cavities which permits the tampon to be held in position, minimizing the chances for inadvertent and unwanted expulsion of said tampon from the body cavity, particularly from the rectum, into which it has been inserted. It is now also clear that the subject invention allows for the application of medication in liquid form directly to the abnormal surrounding tissue and that such medication is delivered on demand, allowing for more accurate and specific dosage of such medication without the disadvantage of modifying such medication by evaporation or oxidation.

I claim:

1. A tampon with a longitudinal axis for insertion in the longitudinal direction thereof into the cavity of a body in which lips surround the entranceway of the body cavity and walls surround the body cavity inwardly of the lips, said tampon comprising:
   (a) a rigid entry end for insertion into the body cavity through the lips surrounding the entranceway of the body cavity;
   (b) a liquid absorbable, expansible bulb-shaped tampon body extending from said entry end, said tampon body being constructed to expand radially outward from the longitudinal axis of said tampon after absorbing liquid, said bulb-shaped tampon body being formed with an ovate portion and a neck portion; and
   (c) a rupturable container with liquid medicant therein disposed within the ovate portion of said tampon body, said container being rupturable to release the liquid medicant therein to be absorbed by said tampon body for expanding said tampon body radially outward from the longitudinal axis of said tampon, after said tampon is inserted into the body cavity, the lips surrounding the entranceway of said body cavity grasp said neck portion of said tampon body and the expanded ovate portion of said tampon body with absorbed liquid medicant contacts the walls surrounding the body cavity inwardly of the lips surrounding the entranceway of the body cavity to apply liquid medicant to the walls surrounding the body cavity.

2. A tampon as claimed in claim 1 and further comprising an absorbable envelope surrounding said tampon body to limit the extent of expansion of said tampon body after said tampon body absorbs liquid medicant.

3. A tampon as claimed in claim 1 wherein said neck portion of said tampon body expands radially outward from the longitudinal axis of said tampon after said tampon body absorbs the liquid medicant for applying liquid medicant to the lips grasping the neck portion of the tampon body.

4. A tampon as claimed in claim 3 and further comprising an absorbable bulb-shaped envelope surrounding the bulb-shaped tampon body, said envelope including an ovate portion surrounding the ovate portion of said tampon body and a neck portion surrounding the neck portion of said tampon body to limit the extent of expansion of said tampon body after said tampon body absorbs liquid medicant.

5. A tampon as claimed in claim 1 and further comprising a protector integrally formed with the neck portion of said tampon body and projecting radially outward from the longitudinal axis of said tampon beyond said neck portion of said tampon body to protect the user from soiling clothing resulting from substances discharged through the lips surrounding the entranceway to the body cavity.

6. A tampon as claimed in claim 4 and further comprising a protector integrally formed with the neck portions of said tampon body and said envelope and projecting radially outward from the longitudinal axis of said tampon beyond said neck portions of said tampon body and said envelope to protect the user from soiling clothing resulting from substances discharged through the lips surrounding the entranceway to the body cavity.

7. A tampon as claimed in claim 5 wherein said protector comprises absorbable material facing said lips and impervious material forming an outer layer thereof.

8. A tampon as claimed in claim 6 wherein said protector comprises absorbable material facing said lips and impervious material forming an outer layer thereof.

9. A tampon as claimed in claim 1 wherein said rigid entry end has a conical configuration with a base and said tampon body extends from the base of said entry end.

10. A tampon as claimed in claim 4 wherein said rigid entry end has a conical configuration with a base and said tampon body extends from the base of said entry end.

* * * * *